US010539513B2

(12) United States Patent
Moore

(10) Patent No.: US 10,539,513 B2
(45) Date of Patent: Jan. 21, 2020

(54) WASTE DETECTION

(71) Applicant: GOJO Industries, Inc., Akron, OH (US)

(72) Inventor: Mark W. Moore, Aurora, OH (US)

(73) Assignee: GOJO Industries, Inc., Akron, OH (US)

(*) Notice: Subject to any disclaimer, the term of this patent is extended or adjusted under 35 U.S.C. 154(b) by 0 days.

(21) Appl. No.: 16/186,906

(22) Filed: Nov. 12, 2018

(65) Prior Publication Data

US 2019/0079024 A1 Mar. 14, 2019

Related U.S. Application Data

(63) Continuation of application No. 15/686,635, filed on Aug. 25, 2017, now Pat. No. 10,126,249, which is a continuation of application No. 15/152,667, filed on May 12, 2016, now Pat. No. 9,746,425.

(60) Provisional application No. 62/160,357, filed on May 12, 2015.

(51) Int. Cl.
  *G01N 21/64* (2006.01)
  *G01N 21/94* (2006.01)
  *G01N 21/84* (2006.01)
  *G01N 21/00* (2006.01)
  (Continued)

(52) U.S. Cl.
  CPC ............ *G01N 21/94* (2013.01); *G01N 21/00* (2013.01); *G01N 21/63* (2013.01); *G01N 21/64* (2013.01); *G01N 21/84* (2013.01); *G01N 21/88* (2013.01); *G01N 21/8806* (2013.01); *G01N 2201/127* (2013.01); *G01N 2201/12746* (2013.01)

(58) Field of Classification Search
  CPC ........ G01N 21/94; G01N 21/84; G01N 21/64; G01N 21/8806; G01N 2201/12746; G01N 21/88; G01N 21/00; G01N 21/63; G01N 2201/127
  See application file for complete search history.

(56) References Cited

U.S. PATENT DOCUMENTS

| 6,838,887 B2 | 1/2005 | Denen et al. |
| 7,570,067 B2 | 8/2009 | Denen et al. |
| 7,783,380 B2 | 8/2010 | York et al. |

(Continued)

FOREIGN PATENT DOCUMENTS

| CN | 203207940 U | 9/2013 |
| CN | 103835355 A | 6/2014 |

(Continued)

*Primary Examiner* — Kiho Kim
(74) *Attorney, Agent, or Firm* — Cooper Legal Group, LLC

(57) ABSTRACT

One or more techniques and/or systems are provided for waste object detection. For example, a waste alert component is configured to emit ultraviolet light towards a waste detection zone, such as a bathroom floor or countertop. If a waste object, such as a paper towel or other object with a fluoresce property, exists within the waste detection zone, then the waste alert component may detect an increase in light due to the waste object fluorescing visible light in response to the ultraviolet light. If the increase in light intensity exceeds a detection threshold, then the waste alert component may provide a waste detection alert that the waste object exists within the waste detection zone (e.g., a message may be sent to a housekeeper that paper towel waste in on the bathroom countertop).

20 Claims, 12 Drawing Sheets

(51) Int. Cl.
    *G01N 21/63*     (2006.01)
    *G01N 21/88*     (2006.01)

(56) References Cited

U.S. PATENT DOCUMENTS

| | | |
|---|---|---|
| 8,160,742 B2 | 4/2012 | Goerg et al. |
| 8,919,233 B2 | 12/2014 | Lewis et al. |
| 8,970,391 B2 | 3/2015 | Hoekstra |
| 2013/0208452 A1 | 8/2013 | Maxwell |
| 2013/0240554 A1 | 9/2013 | Strahlin et al. |

FOREIGN PATENT DOCUMENTS

| | | | | |
|---|---|---|---|---|
| GB | 726493 A | * | 3/1955 | ........... G01N 21/276 |
| WO | 2009105375 A1 | | 8/2009 | |

* cited by examiner

WASTE DETECTION

CROSS-REFERENCE TO RELATED APPLICATIONS

This application claims priority to and is a continuation of U.S. patent application Ser. No. 15/686,635, filed on Aug. 25, 2017 and titled "WASTE DETECTION," which claims priority to and is a continuation of U.S. patent application Ser. No. 15/152,667, filed on May 12, 2016 and titled "WASTE DETECTION," which claims priority to U.S. Provisional Patent Application No. 62/160,357, filed on May 12, 2015, all of which are incorporated herein by reference.

TECHNICAL FIELD

The instant application is generally directed towards systems and techniques for waste object detection. In particular, a waste alert component may detect the presence of a waste object, such as a paper towel on a bathroom floor, based upon visible light fluoresced by the waste object in response to ultraviolet light.

BACKGROUND

Many buildings and locations employ sanitary devices, such as soap dispensers, paper towel dispensers, toilet paper dispenser, air fresheners, etc., to improve sanitization. A housekeeper may routinely clean such locations by refilling dispensers, cleaning trash off of countertops and floors, sanitizing surfaces, etc. Unfortunately, paper towels, toilet paper, and/or other waste objects may be discarded or overflow onto the countertops and floors before routine maintenance is scheduled, which may be unsightly for users. For example, a trashcan within a bathroom may overfill such that paper towels overflow onto a countertop. Thus, a user may issue a complaint regarding the bathroom being unclean. Accordingly, it may be advantageous to detect waste objects within various location such as bathrooms, near trashcans (e.g., a trashcan in a park, a mall food court, a cafeteria, etc.), or other locations where waste objects may be undesirably located.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for waste objection are provided herein. A waste detection component comprises an ultraviolet light source configured to emit ultraviolet light towards a waste detection zone (e.g., an area on a bathroom countertop, a floor, an area near a trashcan, etc.). In an example, a visible light filter may be optionally positioned between the ultraviolet light source and the waste detection zone to filter visible light emitted from the ultraviolet light source (e.g., so that a user of a bathroom does not see light emitted from the ultraviolet light source). The waste detection component comprises a light detection component configured to measure light intensity of light impinging on the light detection component. In an example, an ultraviolet light filter may be optionally positioned between the light detection component and the waste detection zone. The ultraviolet light filter is configured to filter ultraviolet light from reaching the light detection component.

The waste detection component comprises a waste identification component configured to obtain an initial light intensity measurement from the light detection component while the ultraviolet light source is off. The waste identification component is configured to obtain a light intensity measurement from the light detection component while the ultraviolet light source is turned on. The waste identification component is configured to determine a light intensity change based upon a difference between the initial light intensity measurement and the light intensity measurement. The waste identification component may compare the light intensity change to a detection threshold. In an example, the waste identification component may normalize the detection threshold based upon a determination as to whether an ambient light is on or off. Responsive to the light intensity change exceeding the detection threshold, a waste detection alert, that the waste object exists within the waste detection zone, is provided. In an example, multiple light intensity changes may be determined and compared to the detection threshold before the waste detection alert is sent in order to avoid false positive detection of waste objects such as from an ambient light being turned on between the initial light intensity measurement and the light intensity measurement. In an example, the waste detection alert may be sent through an email, a mobile alert, displayed as a user interface element on a map interface depicting a building within which the waste detection component is installed, a wireless signal, a flashing light, an audible alert, or any other type of communication.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
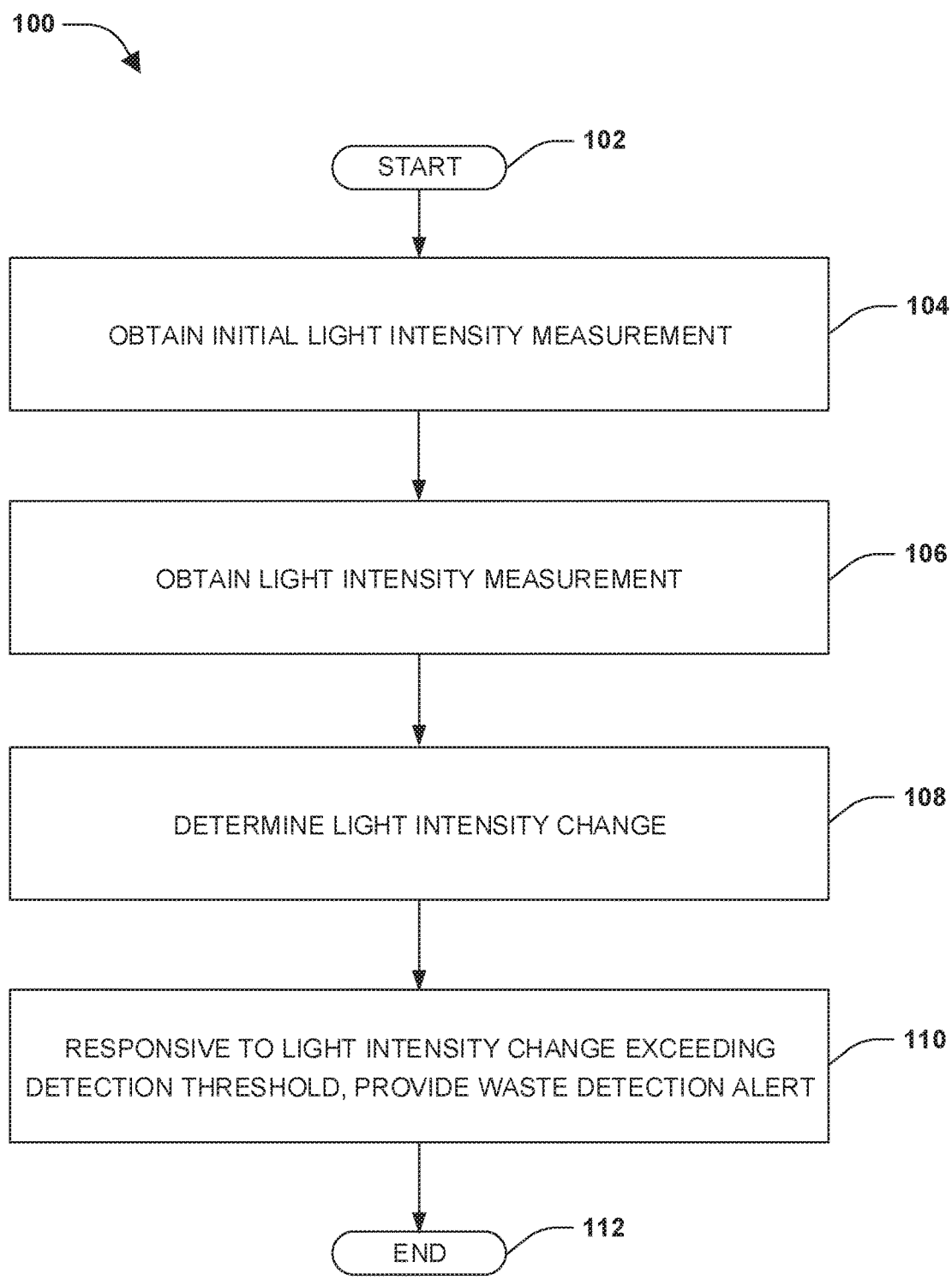
FIG. 1 is a flow diagram illustrating an example method of waste object detection.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

An embodiment of waste object detection is illustrated by an exemplary method 100 of FIG. 1. At 102, the method 100 starts. In an example, a waste alert component may be installed at a location, such as within a bathroom, near a trash receptacle, on a wall above a floor, near a countertop, or near any other location or surface. For example, the waste alert component may be installed along a wall (e.g., installed at a height of 36 inches or less, or any other height) above a cafeteria floor near a trashcan. The waste alert component may be configured to detect a waste object, such as a paper object (e.g., a paper towel, a paper cup, toilet paper, a paper plate, etc.) or any other object that fluoresces visible light in response to ultraviolet light, based upon a measured increase of light resulting from the waste object fluorescing visible light in response to ultraviolet light.

The waste alert component may be calibrated, such as during installation or a learning phase, based upon a surface type of the cafeteria floor and/or ambient lighting within the cafeteria. For example, a detection threshold (e.g., a measured light intensity threshold against which detected light is compared in order to determine whether to trigger a waste detection alert) may be calibrated based upon the surface type of the cafeteria floor on which a waste detection zone is to be defined by the waste alert component. A notification may be received that the cafeteria floor is clear of waste objects. A first calibration light intensity measurement may be obtained from a light detection component of the waste alert component while an ultraviolet light source of the waste alert component is turned off. A second calibration light intensity measurement may be obtained from the light detection component while the ultraviolet light source is turned on. The detection threshold may be calibrated based upon the first calibration light intensity measurement and the second calibration light intensity measurement, such as to compensate for visible light reflected from the cafeteria floor and detected by a light detection component of the waste alert component.

In an example of the calibration, the first calibration light intensity measurement and the second calibration light intensity measurement may be obtained when an ambient light source is off, and thus additional measurements may be obtained for calibration while the ambient light source is on. For example, a third calibration light intensity measurement may be obtained from the light detection component while the ultraviolet light source is turned on and the ambient light source is on. A fourth calibration light intensity measurement may be obtained from the light detection component while the ultraviolet light source is turned off and the ambient light source is on. The detection threshold may be calibrated based upon the third calibration light intensity measurement and the fourth calibration light intensity measurement, such as to compensate for ambient light within the cafeteria (e.g., ambient light reflected off the cafeteria floor and detected by the light detection component). In this way, the waste alert component may be calibrated for various environments.

At 104, an initial light intensity measurement may be obtained from a light detection component while the ultraviolet light source is turned off. The initial light intensity measurement may correspond to a light intensity of ambient light within the cafeteria (e.g., 30% of a total light sensitivity of the light detection component). At 106, a light intensity measurement may be obtained from the lighted detection component while the ultraviolet light source is turned on (e.g., 50% of a total light sensitivity of the light detection component). In an example, the light intensity measurement may be obtained within a threshold timespan from when the initial light intensity measurement was obtained (e.g., within about a few seconds or less).

If the waste detection zone, such as cafeteria floor near the trashcan, does not comprise an object that fluoresces visible light in response to ultraviolet light, then the initial light intensity measurement and the light intensity measurement may be similar (e.g., the light intensity measurement may be 32%). However, if the waste detection zone comprises an object that fluoresces visible light in response to ultraviolet light, then the light intensity measurement may be greater than the initial light intensity measurement (e.g., the light intensity measurement may be 50%). At 108, a light intensity change may be determined based upon the initial light intensity measurement and the light intensity measurement. The light intensity change may indicate a percentage change in detected light by the light detection component (e.g., a 20% increase in detected light intensity).

At 110, responsive to the light intensity change exceeding a detection threshold (e.g., a percentage increase of detected light by the light detection component such as an increase of at least 8% or any other percentage increase in detected light between the initial light intensity measurement and the light intensity measurement), a waste detection alert, that a waste object exists within the waste detection zone, may be provided. In an example, the waste detection alert may be provided once a threshold number of detection cycles (e.g., acquisition and comparison of initial light intensity measurements and light intensity measurements for determination of light intensity changes) indicate that a threshold number of light intensity changes have exceeded the detection threshold. Otherwise, a change in ambient light, such as a light turning on within the cafeteria, between acquisition of the initial light intensity measurement and the light intensity measurement may result in an increase in detected light that may be otherwise trigger a false positive detection that the increase was due to a waste object fluorescing visible light as opposed to merely the ambient light being turned on. In an example, the waste detection alert may be provided through an email, a text message, a radio frequency identification (RFID) signal, a wireless signal, an audible alert, a visible alert, a mobile device alert, etc. The waste detection alert may provide an indication that the waste object was detected within the waste detection zone (e.g., a housekeeper may be alerted to clean the trashcan and/or the floor around the trashcan within the cafeteria). In an example, the waste detection alert may be displayed within a map interface depicting a building, such as the cafeteria, with which the waste alert component is installed (e.g., the housekeeper may access the map interface through a mobile device such as a mobile phone or tablet, and the map interface may display a user interface element indicative of the waste object such as an exclamation point, a red shaded area, a trash icon, or other indicator). In this way, waste detection alerts, indicating waste objects such as objects that fluoresce visible light in response to ultraviolet light, may be provided. At 112, the method 100 ends.

Figure 2:
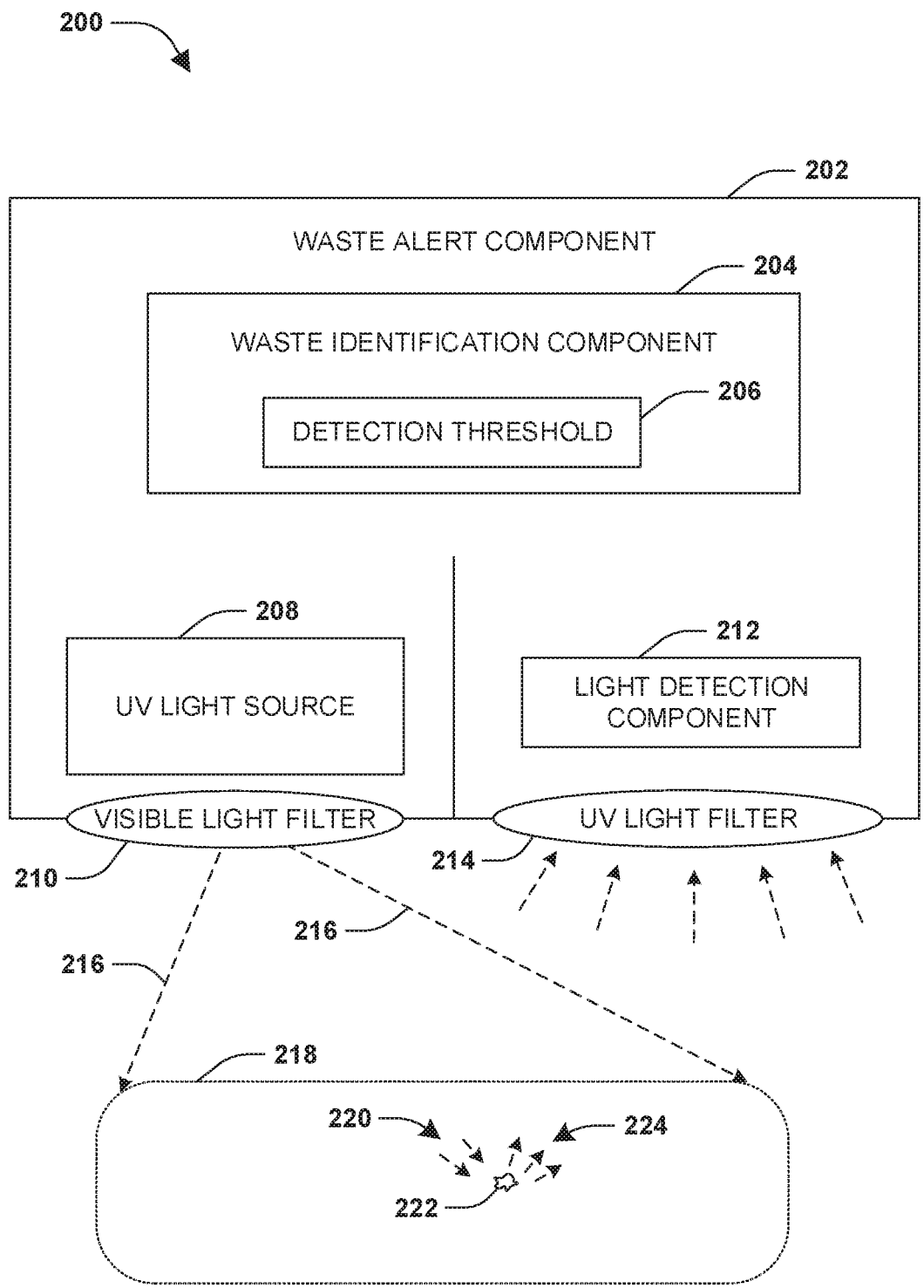
FIG. 2 is a component block diagram illustrating an example system for waste object detection.

FIG. 2 illustrates an example of a system 200 for waste object detection. The system 200 comprises a waste alert component 202 configured to detect a waste object, such as a paper object (e.g., a paper towel, a paper cup, toilet paper, a paper plate, etc.), based upon a detected increase of visible light resulting from the waste object fluorescing visible light in response to ultraviolet light. The waste alert component 202 comprises an ultraviolet light source 208, such as an ultraviolet light emitting diode (LED) array, configured to emit ultraviolet light 216 towards a waste detection zone 218, such as a bathroom countertop, a floor of a bathroom, or any other surface. The waste detection zone 218 may be defined according to any shape and/or size (e.g., based upon a lens configuration of the ultraviolet light source 208 and/or a distance of the ultraviolet light source 208 from the surface on which the waste detection zone 218 is defined), such as a rectangle, a substantially circular shape, a substantially semi-circular shape, a polygon, etc. In an example, a visible light filter 210 is positioned between the ultraviolet light source 208 and the waste detection zone 218. The visible light filter 210 may be configured to filter visible light emitted from the ultraviolet light source 208 (e.g., so that a user of the bathroom does not notice the ultraviolet light source 208 emitting light).

The waste alert component 202 may comprise a light detection component 212, such as a photo detector, configured to measure light intensity of light impinging on the light detection component 212. In an example, an ultraviolet light filter 214 may be positioned between the light detection component 212 and the waste detection zone 218. The ultraviolet light filter 214 may filter ultraviolet light from reaching the light detection component 212. In another example, the light detection component 212 and/or the ultraviolet light source 208 may comprise components with sensitivities in specific wavelength ranges such that the light detection component 212 does not detect or account for ultraviolet light. In another example, the light detection component 212 may be trained to learn thresholds that compensate for detected ultraviolet light (e.g., a detection threshold 206 may be increased to account to detected ultraviolet light).

The waste alert component 202 may comprise a waste identification component 204. The waste identification component 204 may calibrate the detection threshold 206 (e.g., a threshold, such as a 15% increase or more in detected light by the light detection component 212, used to determine whether a waste object is located within the waste detection zone 218) based upon a surface type of the surface within the waste detection zone 218. For example, the waste identification component 204 may obtain calibration light intensity measurements while the ultraviolet light source 208 is on and an ambient light is on, while the ultraviolet light source 208 is off and the ambient light is off, while the ultraviolet light source 208 is on and the ambient light is off, and/or while the ultraviolet light source 208 is off and the ambient light is off. In this way, the calibration light intensity measurements may be used to determine a value (e.g., a percent increase of detected light) for the detection threshold 206, such that a change in measured light intensity between the ultraviolet light source 208 being off and then on may indicate that a waste object is within the waste detection zone and fluoresce visible light when the ultraviolet light source 208 was turned on thus resulting in an increase in measured light intensity (e.g., the light detection component 212 may detect an increase in light when the ultraviolet light source 208 is turned on because a waste object 222 fluoresces visible light 224 in response to ultraviolet light 220 from the ultraviolet light source 208). In an example, the detection threshold 206 may be dependent upon the surface type of the surface, ultraviolet light intensity of the ultraviolet light 216, a size of the waste detection zone 218 and/or a size of a waste object, and/or a fluoresce effect of a type of waste object to be detected. In an example, the detection threshold 206 may be set based upon a sensitivity adjustment parameter (e.g., a sensitivity may be decreased to mitigate false positive detection of waste objects).

In an example of performing a detection cycle for identifying waste objects within the waste detection zone 218 based upon visible light fluoresced from waste objects, the waste identification component 204 may obtain an initial light intensity measurement from the light detection component 212 while the ultraviolet light source 208 is off. For example, the initial light intensity measurement may correspond to 45% of a total light sensitivity of the light detection component 212 (e.g., ambient light may account for the initial light intensity measurement). The waste identification component 204 may obtain a light intensity measurement from the light detection component 212 while the ultraviolet light source 208 is on. For example, the light intensity measurement may correspond to 68% of the total light sensitivity of the light detection component (e.g., a 23% increase in detected light) because the waste object 222 fluoresced visible light 224 in response to ultraviolet light 220.

The waste identification component 204 may determine a light intensity change, such as the 23% increase in detected light, based upon the initial light intensity measurement of 45% and the light intensity measurement of 68%. In an example, the detection threshold 206 may be normalized based upon whether an ambient light is on or off (e.g., the 15% threshold increase in detected light may be applied to the 45% initial light intensity measurement due to the ambient light being on, and thus the detection threshold may be set to a 15% increase over the 45% initial light intensity measurement). The waste identification component 204 may determine that the light intensity change of 23%, over the initial light intensity measurement of 45%, exceeds the detection threshold of 15% over the initial light intensity measurement of 45%. Accordingly, the waste identification component 204 may provide a waste detection alert that the waste object 222 exists within the waste detection zone, such as an email, a text message, a radio frequency identification signal, a wireless signal, an audible alert, a visible alert (e.g., a flashing light), a mobile device alert, display of a waste detection alert user interface element within a map interface depicting a building within which the waste alert component 202 is located, etc.

In an example, the waste identification component 204 may refrain from sending the waste detection alert until a threshold number of light intensity changes exceed the detection threshold 206, which may mitigate false positive detections of waste objects such as where an ambient light source may be turned on between acquisition of the initial light intensity measurement and the light intensity measurement and thus an increase in ambient light may be incorrectly detected as visible light fluoresced from a waste object. For example, the waste identification component 204 may perform a sequence of multiple detection cycles, where initial light intensity measurements are obtained while the ultraviolet light source 208 is off, light intensity measurements are obtained while the ultraviolet light source 208 is on, and light intensity changes are determined based upon differences of corresponding initial light intensity measurements and light intensity measurements.

FIGS. 3A-3D illustrate examples of a system 302 for waste object detection. The system 302 may comprise a waste alert component 317 installed on a wall 304 of a bathroom. The bathroom may comprise a sink 314, a bathroom countertop 312, a paper towel dispenser 316, a trashcan 328, a floor 301, a first ambient light source 306, a second ambient light source 308, a mirror 310, and/or other objects. The waste alert component 317 may comprise an ultraviolet light source 320, a visible light filter 322, a light detection component 324, an ultraviolet light filter 326, and/or a waste identification component 318.

Figure 3A:
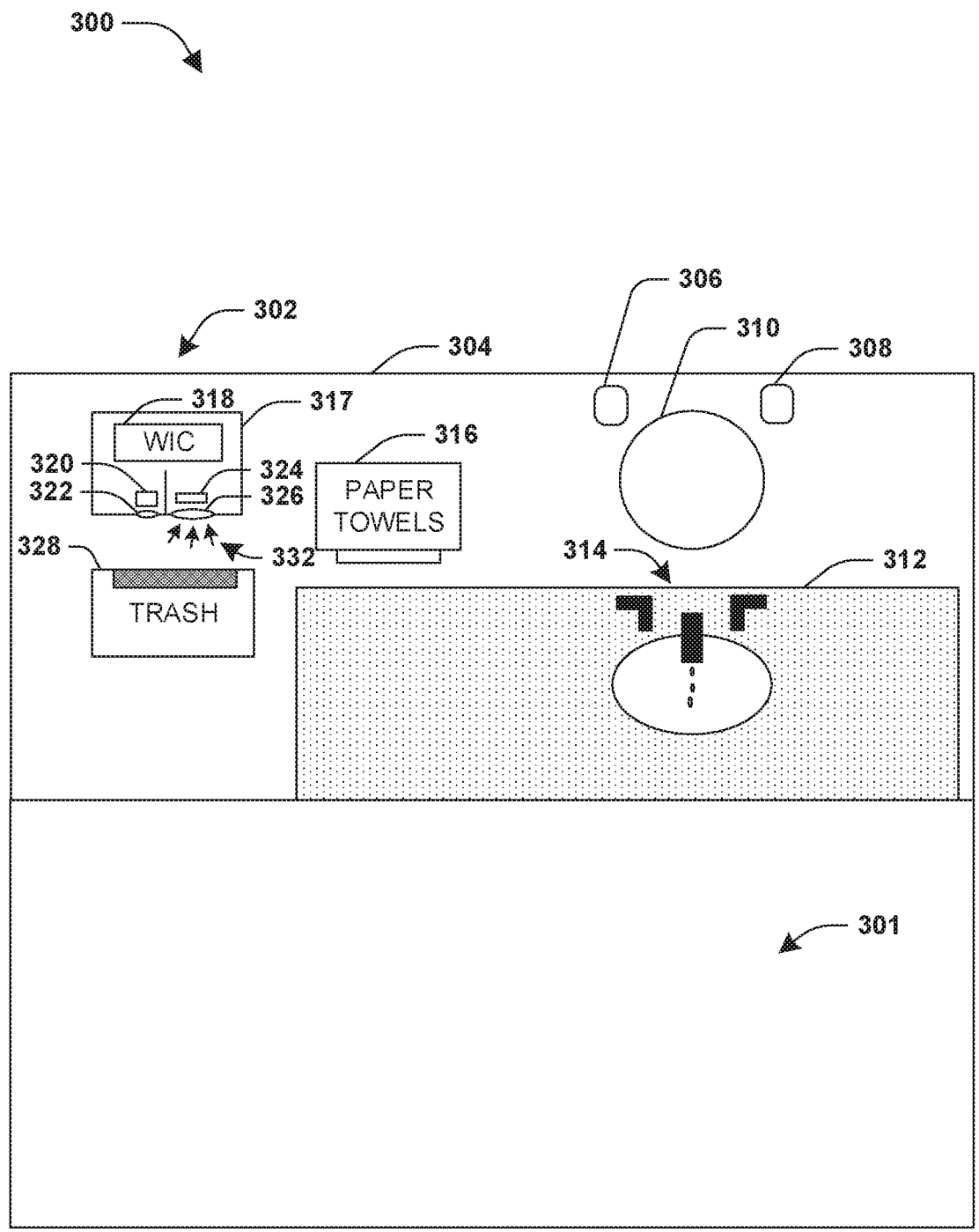
FIG. 3A is a component block diagram illustrating an example system for waste object detection, where a first calibration light intensity measurement is obtained.
Figure 3B:
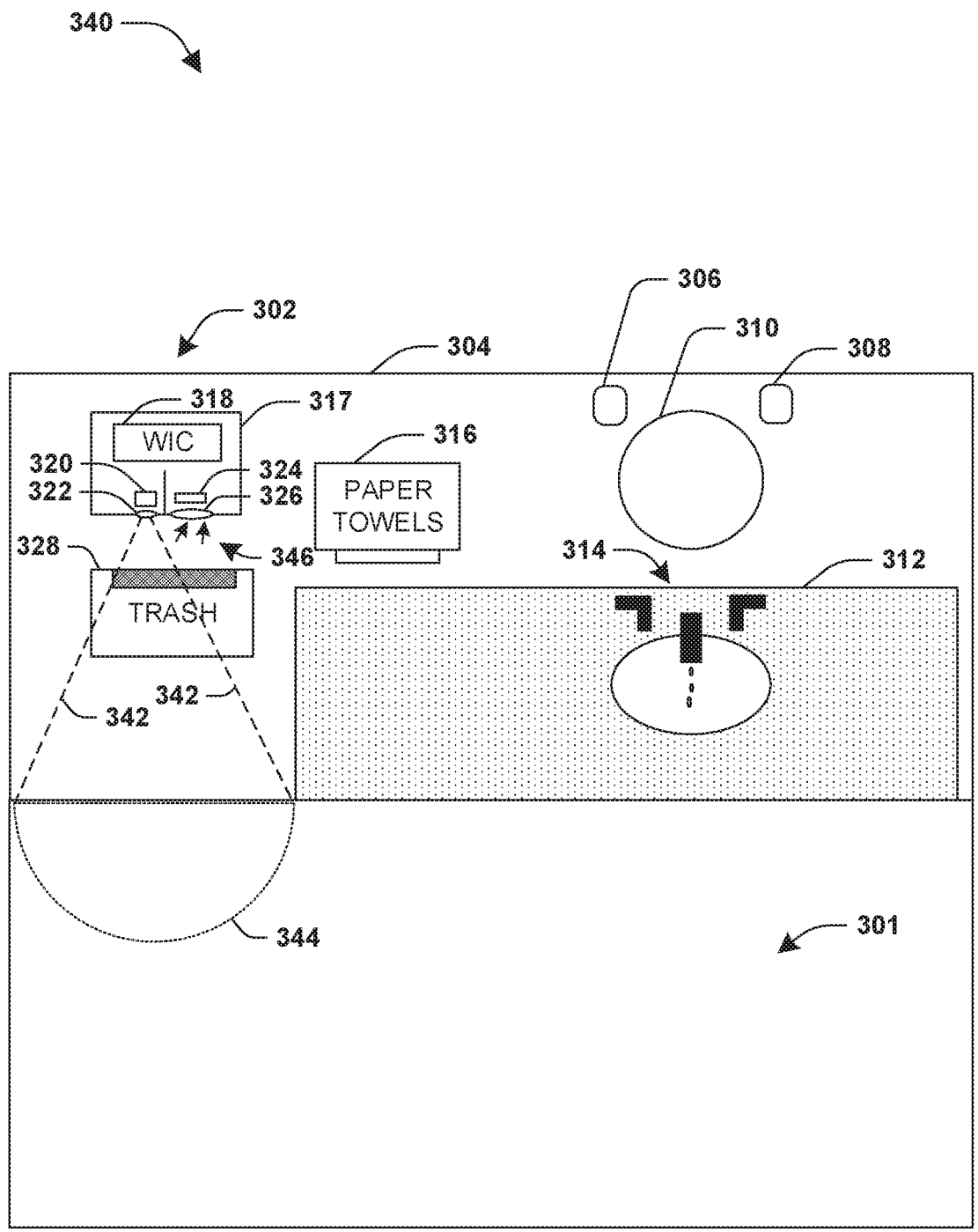
FIG. 3B is a component block diagram illustrating an example system for waste object detection, where a second calibration light intensity measurement is obtained.

The waste identification component 318 performing a calibration (e.g., calibration based upon a surface type of a surface, such as the floor 301, over which a waste detection zone 344 is to be defined), such as to determine a detection threshold for detecting waste objects and/or normalization parameters to compensate for ambient light. In an example, the calibration may be initiated based upon a calibration command or learning phase, such as where a notification that a surface is clear of waste objects, such as the floor 301. FIG. 3A illustrates an example 300 of the waste identification component 318 obtaining 332 a first calibration light intensity measurement from the light detection component 324 while the ultraviolet light source 320, the first ambient light source 306, and the second ambient light source 308 are turned off. FIG. 3B illustrates an example 340 of the waste identification component 318 obtaining 346 a second calibration light intensity measurement from the light detection component 324 while the ultraviolet light source 320 is turned on to emit ultraviolet light 342 towards the waste detection zone 344, and while the first ambient light source 306 and the second ambient light source 308 are turned off.

Figure 3C:
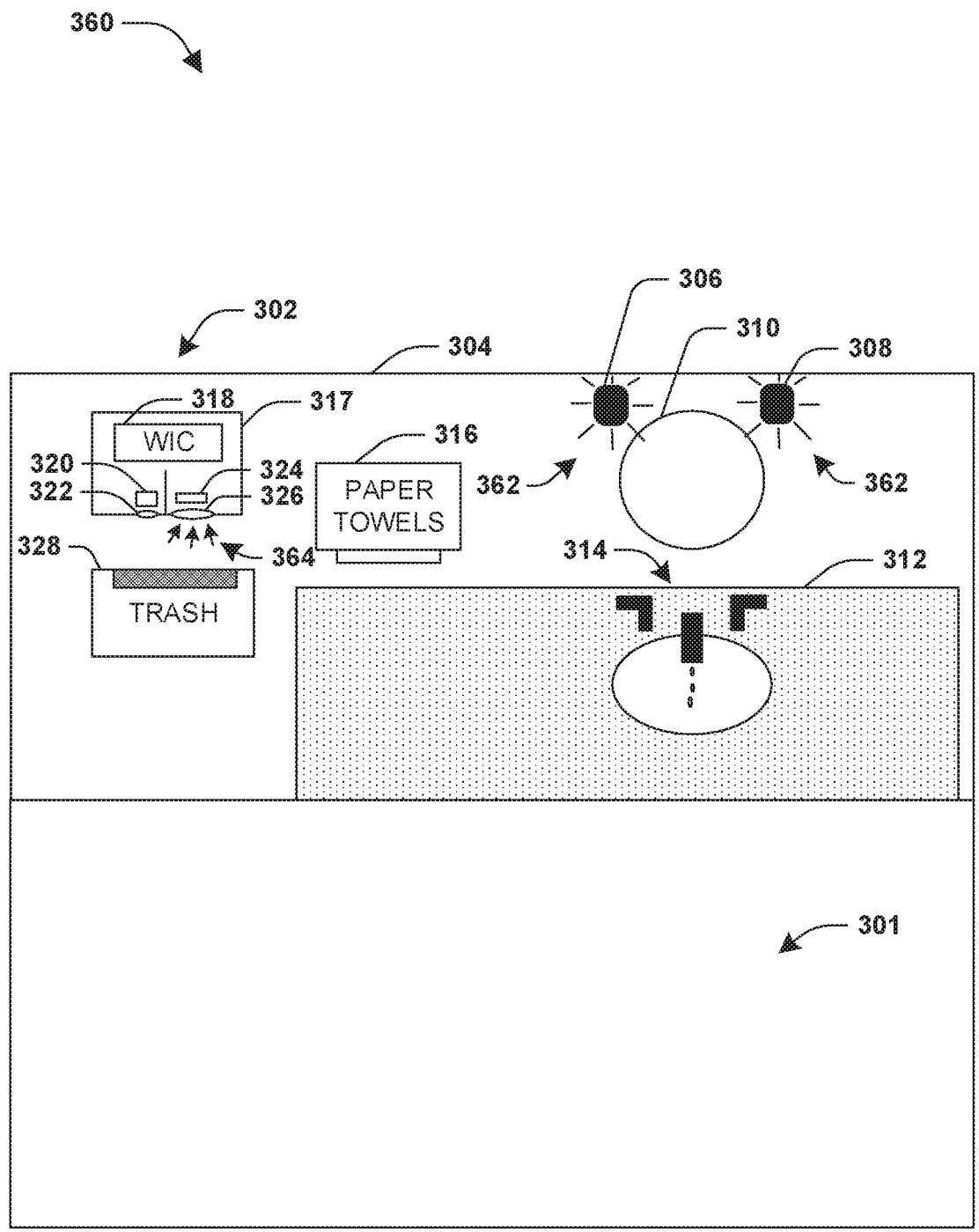
FIG. 3C is a component block diagram illustrating an example system for waste object detection, where a third calibration light intensity measurement is obtained.
Figure 3D:
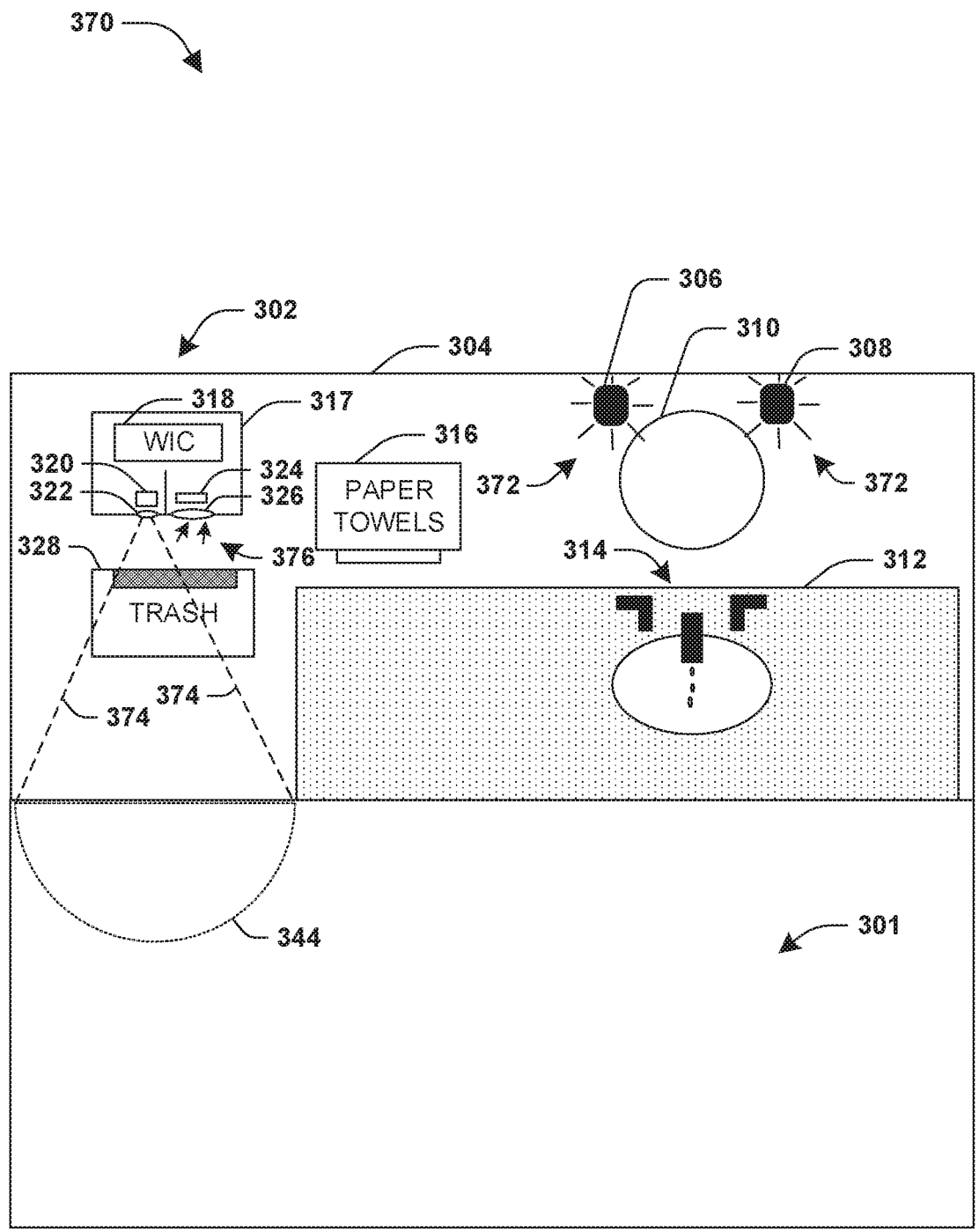
FIG. 3D is a component block diagram illustrating an example system for waste object detection, where a fourth calibration light intensity measurement is obtained.

FIG. 3C illustrates an example 360 of the waste identification component 318 obtaining 364 a third calibration light intensity measurement from the light detection component 324 while the ultraviolet light source 320 is turned off, and while the first ambient light source 306 and the second ambient light source 308 are turned on and thus emitting ambient light 362. FIG. 3D illustrates an example 370 of the waste identification component 318 obtaining 376 a fourth calibration light intensity measurement from the light detection component 324 while the ultraviolet light source 320 is turned on to emit ultraviolet light 374 towards the waste detection zone 344, and while the first ambient light source 306 and the second ambient light source 308 are turned on and thus emitting ambient light 372. In this way, the waste identification component 318 may calibrate the detection threshold using one or more of the calibration light intensity measurements to adjust for ambient light and/or the surface type of the floor 301.

Figure 4A:
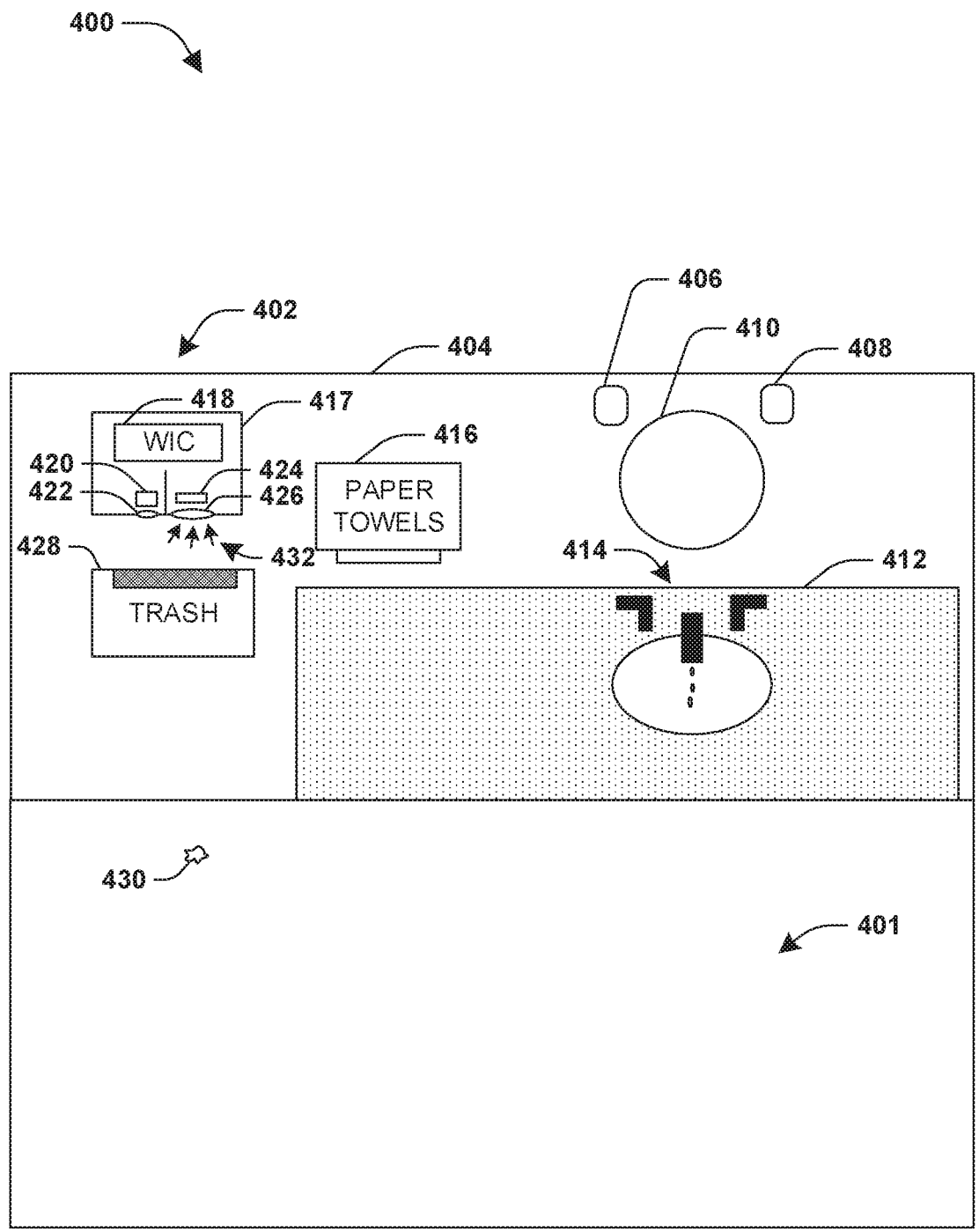
FIG. 4A is a component block diagram illustrating an example system for waste object detection, where an initial light intensity measurement is obtained.
Figure 4B:
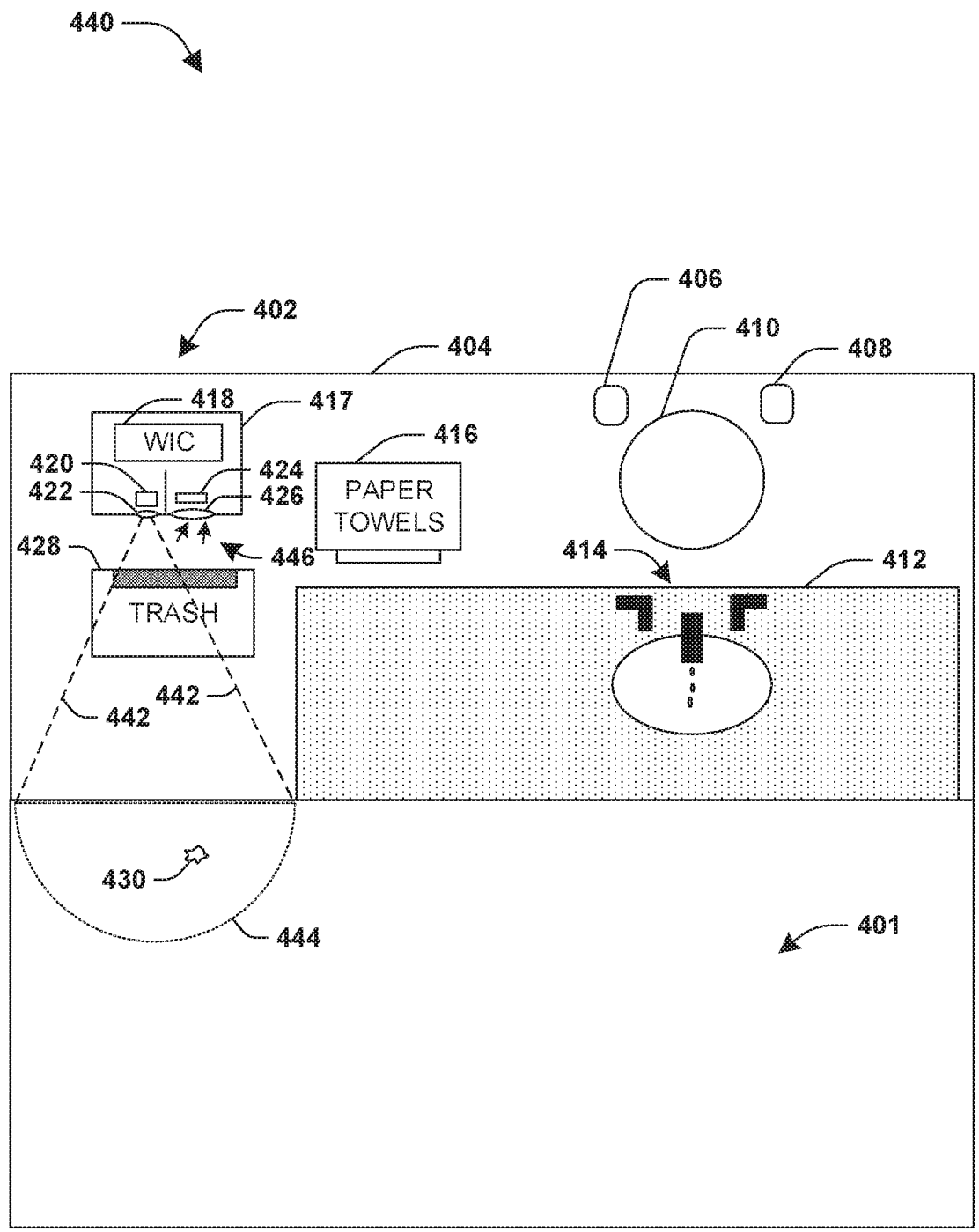
FIG. 4B is a component block diagram illustrating an example system for waste object detection, where a light intensity measurement is obtained and a waste detection alert is provided.

FIGS. 4A-4B illustrate examples of a system 402 for waste object detection. The system 402 may comprise a waste alert component 417 installed on a wall 404 of a bathroom. The bathroom may comprise a sink 414, a bathroom countertop 412, a paper towel dispenser 416, a trashcan 428, a floor 401, a first ambient light source 406, a second ambient light source 408, a mirror 410, and/or other objects. The waste alert component 417 may comprise an ultraviolet light source 420, a visible light filter 422, a light detection component 424, an ultraviolet light filter 426, and/or a waste identification component 418.

FIG. 4A illustrates an example 400 of the waste identification component 418 obtaining 432 an initial light intensity measurement from the light detection component 424 while the ultraviolet light source 420, the first ambient light source 406, and the second ambient light source 408 are turned off. For example, the initial light intensity measurement may correspond to 5% of a total light sensitivity of the light detection component 424. FIG. 4B illustrates an example 440 of the waste identification component 418 obtaining 446 a light intensity measurement from the light detection component 424 while the ultraviolet light source 420 is turned on to emit ultraviolet light 442 towards a waste detection zone 444, and while the first ambient light source 406 and the second ambient light source 408 are turned off. For example, the light intensity measurement may correspond to 20% of the total light sensitivity of the light detection component 424 because a waste object 430, such as a paper towel, may have fluoresced and emitted visible light in response to the ultraviolet light 442.

The waste identification component 418 may determine a light intensity change of 15% based upon a difference between the initial light intensity measurement of 5% and the light intensity measurement of 20%. The waste identification component 418 may determine that the light intensity change of 15% may exceed a detection threshold of a 10% increase change in light intensity. Accordingly, the waste identification component 418 may provide a waste detection alert that the waste object 430 exists within the waste detection zone 444.

Figure 5A:
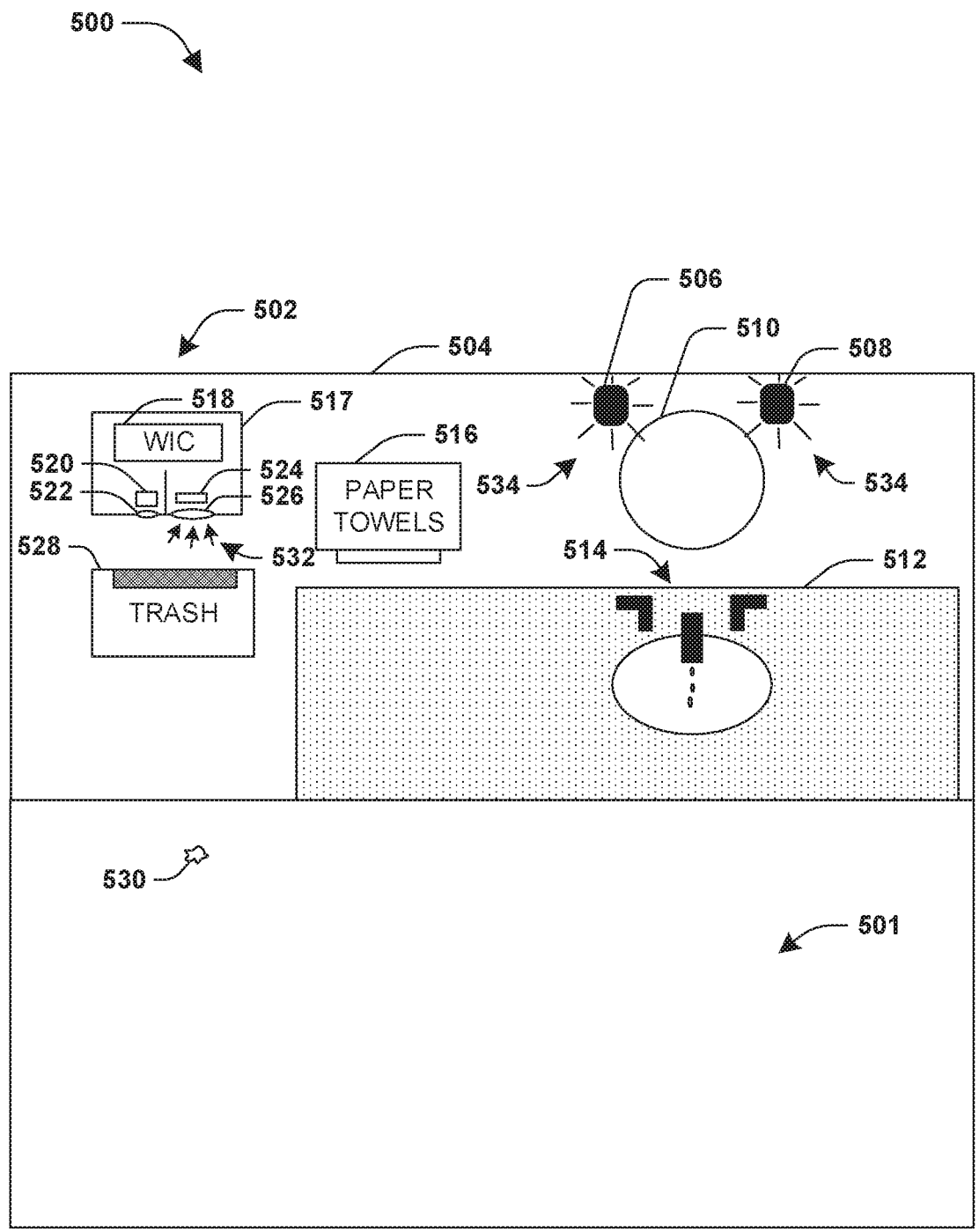
FIG. 5A is a component block diagram illustrating an example system for waste object detection, where an initial light intensity measurement is obtained.
Figure 5B:
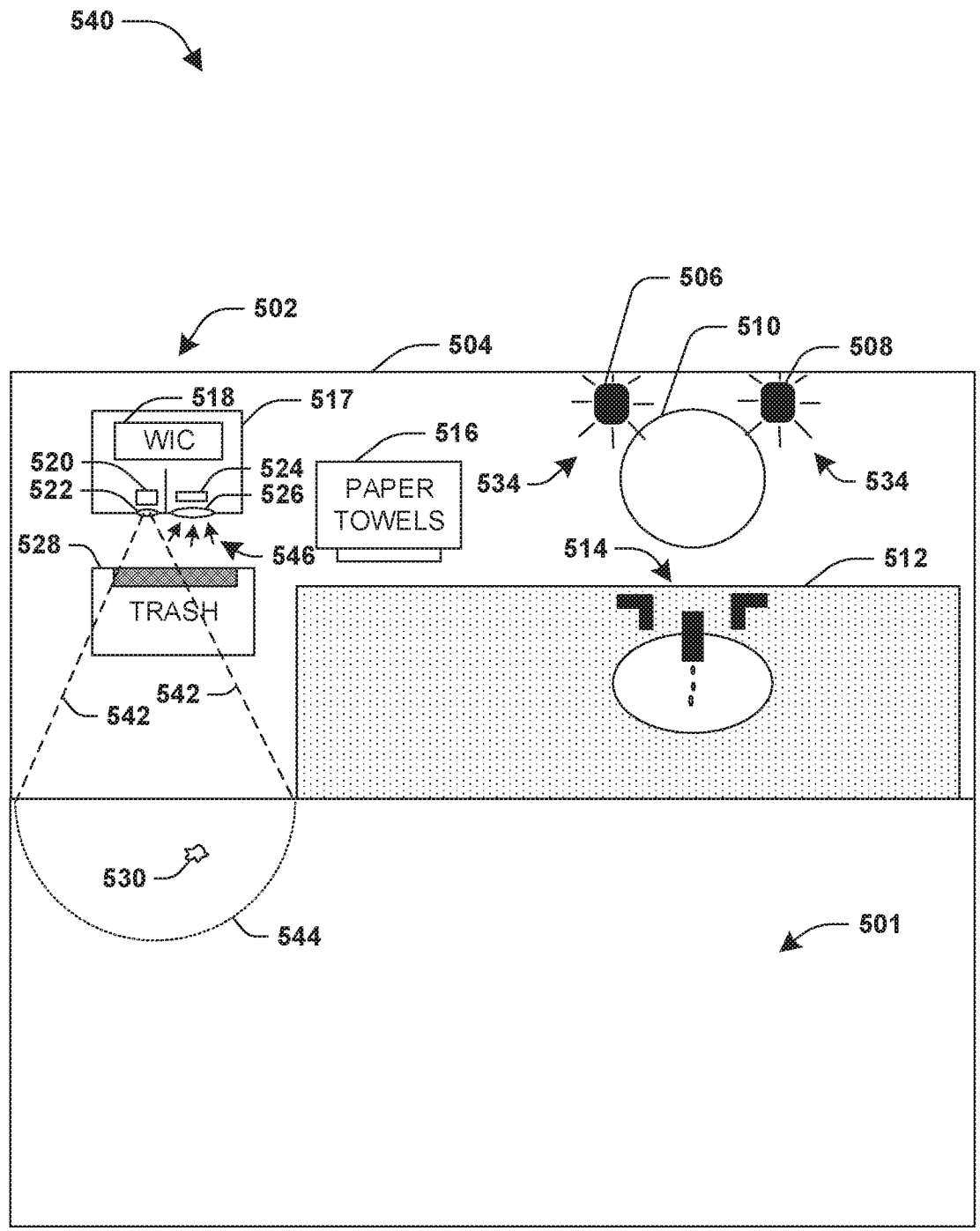
FIG. 5B is a component block diagram illustrating an example system for waste object detection, where a light intensity measurement is obtained and a waste detection alert is provided.

FIGS. 5A-5B illustrate examples of a system 502 for waste object detection. The system 502 may comprise a waste alert component 517 installed on a wall 504 of a bathroom. The bathroom may comprise a sink 514, a bathroom countertop 512, a paper towel dispenser 516, a trashcan 528, a floor 501, a first ambient light source 506, a second ambient light source 508, a mirror 510, and/or other objects. The waste alert component 517 may comprise an ultraviolet light source 520, a visible light filter 522, a light detection component 524, an ultraviolet light filter 526, and/or a waste identification component 518.

FIG. 5A illustrates an example 500 of the waste identification component 518 obtaining 532 an initial light intensity measurement from the light detection component 524 while the ultraviolet light source 520 is turned off, and while the first ambient light source 506 and the second ambient light source 508 are turned on to emit visible light 534. For example, the initial light intensity measurement may correspond to 55% of a total light sensitivity of the light detection component 524 based upon the visible light 534. FIG. 5B illustrates an example 540 of the waste identification component 518 obtaining 546 a light intensity measurement from the light detection component 524 while the ultraviolet light source 520 is turned on to emit ultraviolet light 542 towards a waste detection zone 544, and while the first ambient light source 506 and the second ambient light source 508 are turned on to emit visible light 534. For example, the light intensity measurement may correspond to 77% of the total light sensitivity of the light detection component 524 because a waste object 530, such as a paper towel, may have fluoresced and emitted visible light in response to the ultraviolet light 542.

The waste identification component 518 may determine a light intensity change of 22% based upon a difference between the initial light intensity measurement of 55% and the light intensity measurement of 77%. The waste identification component 518 may determine that the light intensity change of 22% may exceed a detection threshold of a 10% increase change in light intensity (e.g., the detection threshold may be normalized based upon the ambient light 534). Accordingly, the waste identification component 518 may provide a waste detection alert that the waste object 530 exists within the waste detection zone 544.

Figure 6A:
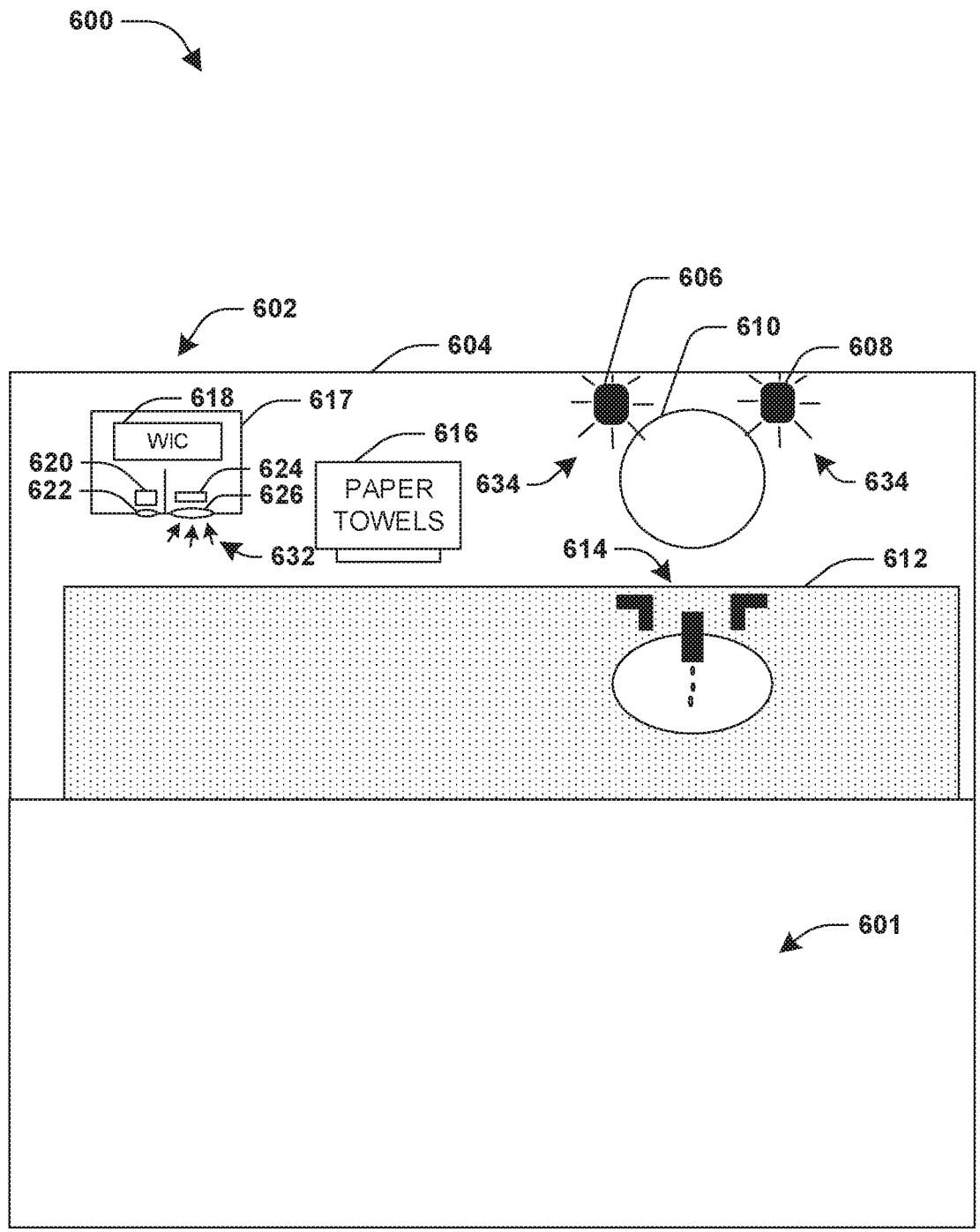
FIG. 6A is a component block diagram illustrating an example system for waste object detection, where an initial light intensity measurement is obtained.
Figure 6B:
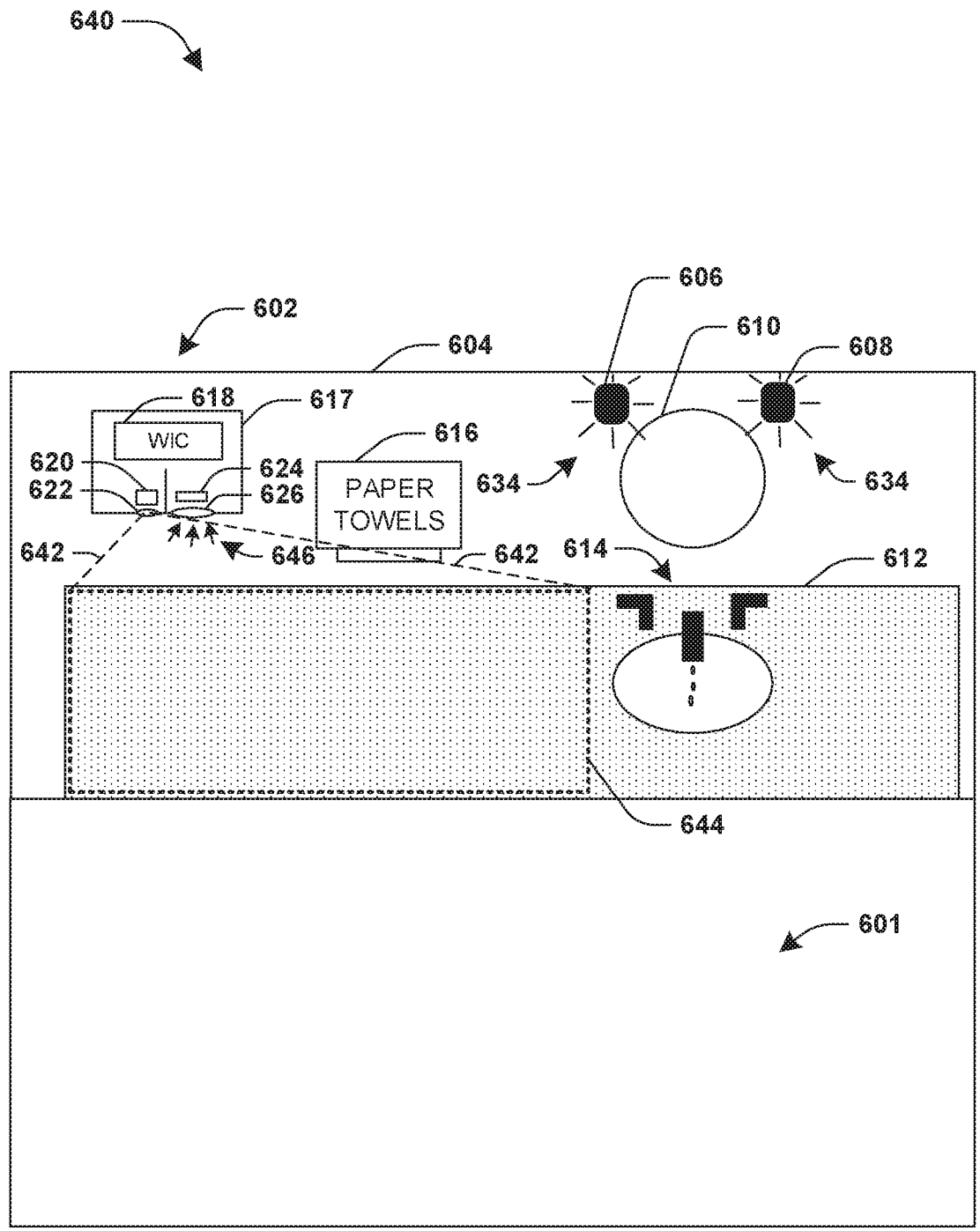
FIG. 6B is a component block diagram illustrating an example system for waste object detection, where a light intensity measurement is obtained and a waste detection alert is not provided.

FIGS. 6A-6B illustrate examples of a system 602 for waste object detection. The system 602 may comprise a waste alert component 617 installed along a wall 604 and over a bathroom over bathroom countertop 612. The bathroom may comprise a sink 614, the bathroom countertop 612, a paper towel dispenser 616, a trashcan 628, a floor 601, a first ambient light source 606, a second ambient light source 608, a mirror 610, and/or other objects. The waste alert component 617 may comprise an ultraviolet light source 620, a visible light filter 622, a light detection component 624, an ultraviolet light filter 626, and/or a waste identification component 618.

FIG. 6A illustrates an example 600 of the waste identification component 618 obtaining 632 an initial light intensity measurement from the light detection component 624 while the ultraviolet light source 620 is turned off, and while the first ambient light source 606 and the second ambient light source 608 are turned on to emit visible light 634. For example, the initial light intensity measurement may correspond to 55% of a total light sensitivity of the light detection component 624 based upon the visible light 634. FIG. 6B illustrates an example 640 of the waste identification component 618 obtaining 646 a light intensity measurement from the light detection component 624 while the ultraviolet light source 620 is turned on to emit ultraviolet light 642 towards a waste detection zone 644, and while the first ambient light source 606 and the second ambient light source 608 turned on to emit visible light 634. For example, the light intensity measurement may correspond to 57% of the total light sensitivity of the light detection component 624 (e.g., because no objects, such as paper towels or other waste objects that fluoresce visible light in response to the ultraviolet light 642, are within the waste detection zone 644, a relatively smaller increase, if any, of light may be detected by the light detection component 624).

The waste identification component 618 may determine a light intensity change of 2% based upon a difference between the initial light intensity measurement of 55% and the light intensity measurement of 57%. The waste identification component 618 may determine that the light intensity change of 2% does not exceed a detection threshold of a 10% increase change in light intensity (e.g., the detection threshold may be normalized based upon the ambient light 634). Accordingly, the waste identification component 618 may refrain from providing a waste detection alert because the light intensity change of 2% indicates that no waste object exists within the waste detection zone 644.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

It will be appreciated that layers, features, elements, etc. depicted herein are illustrated with particular dimensions relative to one another, such as structural dimensions or orientations, for example, for purposes of simplicity and ease of understanding and that actual dimensions of the same differ substantially from that illustrated herein, in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a" and "an" as used in this application are generally to be construed to mean "one or more" unless specified otherwise or clear from context to be directed to a singular form. Also, at least one of A and B or the like generally means A or B or both A and B. Furthermore, to the extent that "includes", "having", "has", "with", or variants thereof are used in either the detailed description or the claims, such terms are intended to be inclusive in a manner similar to "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A system for waste object detection, comprising:
   a photo detector configured to measure light intensity of light impinging on the photo detector; and
   a waste identification component configured to:
      calibrate a detection threshold based upon a surface type of a surface within a waste detection zone;
      determine a light intensity change based upon an initial light intensity measurement by the photo detector and a subsequent light intensity measurement by the photo detector; and
      responsive to the light intensity change exceeding the detection threshold, provide a waste detection alert that a waste object exists within the waste detection zone.

2. The system of claim 1, the waste identification component configured to:

send the waste detection alert to a user through at least one of an email, a text message, a radio frequency identification (RFID) signal, a wireless signal, an audible alert, a visible alert, or a mobile device alert.

3. The system of claim 1, the waste detection zone corresponding to at least one of a surface of a bathroom countertop or a floor of a bathroom.

4. The system of claim 1, the waste identification component configured to:
 display the waste detection alert within a map interface depicting a building within which a waste alert component is located.

5. A system for waste object detection, comprising:
 a photo detector configured to measure light intensity of light impinging on the photo detector; and
 a waste identification component configured to:
  determine a light intensity change based upon an initial light intensity measurement by the photo detector and a subsequent light intensity measurement by the photo detector;
  evaluate the initial light intensity measurement to determine whether an ambient light source is on or off;
  normalize a detection threshold based upon whether the ambient light source is on or off; and
  responsive to the light intensity change exceeding the detection threshold, provide a waste detection alert that a waste object exists within a waste detection zone.

6. The system of claim 5, the waste identification component configured to:
 send the waste detection alert to a user through at least one of an email, a text message, a radio frequency identification (RFID) signal, a wireless signal, an audible alert, a visible alert, or a mobile device alert.

7. The system of claim 5, the waste detection zone corresponding to at least one of a surface of a bathroom countertop or a floor of a bathroom.

8. The system of claim 5, the waste identification component configured to:
 display the waste detection alert within a map interface depicting a building within which a waste alert component is located.

9. A system for waste object detection, comprising:
 a photo detector configured to measure light intensity of light impinging on the photo detector; and
 a waste identification component configured to:
  determine a light intensity change based upon an initial light intensity measurement by the photo detector and a subsequent light intensity measurement by the photo detector;
  determine a detection threshold based upon a fluoresce effect of a type of waste object to be detected; and
  responsive to the light intensity change exceeding the detection threshold, provide a waste detection alert that a waste object exists within a waste detection zone.

10. The system of claim 9, the waste identification component configured to:
 send the waste detection alert to a user through at least one of an email, a text message, a radio frequency identification (RFID) signal, a wireless signal, an audible alert, a visible alert, or a mobile device alert.

11. The system of claim 9, the waste detection zone corresponding to at least one of a surface of a bathroom countertop or a floor of a bathroom.

12. The system of claim 9, the waste identification component configured to:
 display the waste detection alert within a map interface depicting a building within which a waste alert component is located.

13. A system for waste object detection, comprising:
 a photo detector configured to measure light intensity of light impinging on the photo detector; and
 a waste identification component configured to:
  perform a sequence of detection cycles, a first detection cycle comprising an initial light intensity measurement by the photo detector and a subsequent light intensity measurement by the photo detector;
  determine one or more light intensity change based upon the sequence of detection cycles; and
  responsive to a threshold number of light intensity changes exceeding a detection threshold during the sequence of detection cycles, provide a waste detection alert that a waste object exists within a waste detection zone, otherwise, refrain from providing the waste detection alert.

14. The system of claim 13, the waste identification component configured to:
 send the waste detection alert to a user through at least one of an email, a text message, a radio frequency identification (RFID) signal, a wireless signal, an audible alert, a visible alert, or a mobile device alert.

15. The system of claim 13, the waste detection zone corresponding to at least one of a surface of a bathroom countertop or a floor of a bathroom.

16. The system of claim 13, the waste identification component configured to:
 display the waste detection alert within a map interface depicting a building within which a waste alert component is located.

17. A system for waste object detection, comprising:
 a photo detector configured to measure light intensity of light impinging on the photo detector; and
 a waste identification component configured to:
  determine a light intensity change based upon an initial light intensity measurement by the photo detector and a subsequent light intensity measurement by the photo detector, the subsequent light intensity measurement corresponding to visible light fluoresced from a waste object based upon ultraviolet light; and
  responsive to the light intensity change exceeding a detection threshold, provide a waste detection alert that the waste object exists within a waste detection zone.

18. The system of claim 17, the waste identification component configured to:
 send the waste detection alert to a user through at least one of an email, a text message, a radio frequency identification (RFID) signal, a wireless signal, an audible alert, a visible alert, or a mobile device alert.

19. The system of claim 17, the waste detection zone corresponding to at least one of a surface of a bathroom countertop or a floor of a bathroom.

20. The system of claim 17, the waste identification component configured to:
 display the waste detection alert within a map interface depicting a building within which a waste alert component is located.

* * * * *